US009585787B2

(12) United States Patent
Woods

(10) Patent No.: US 9,585,787 B2
(45) Date of Patent: Mar. 7, 2017

(54) MULTI-LAYERED HEAT THERAPY AND ELECTROTHERAPY BACK PAD DEVICE

(71) Applicant: John L. Woods, Queens Village, NY (US)

(72) Inventor: John L. Woods, Queens Village, NY (US)

(*) Notice: Subject to any disclaimer, the term of this patent is extended or adjusted under 35 U.S.C. 154(b) by 499 days.

(21) Appl. No.: 13/922,374

(22) Filed: Jun. 20, 2013

(65) Prior Publication Data

US 2013/0345778 A1    Dec. 26, 2013

Related U.S. Application Data

(60) Provisional application No. 61/662,121, filed on Jun. 20, 2012.

(51) Int. Cl.
*A61F 7/08* (2006.01)
*A61F 7/00* (2006.01)
*A61N 1/36* (2006.01)
*A61N 1/04* (2006.01)

(52) U.S. Cl.
CPC ............ *A61F 7/007* (2013.01); *A61N 1/0456* (2013.01); *A61N 1/0492* (2013.01); *A61N 1/36021* (2013.01); *A61F 2007/0024* (2013.01); *A61F 2007/0094* (2013.01); *A61N 1/0476* (2013.01)

(58) Field of Classification Search
CPC ............ A61F 7/007; A61F 2007/0024; A61N 1/0452; A61N 1/0456; A61N 1/0476; A61N 1/36021
See application file for complete search history.

(56) References Cited

U.S. PATENT DOCUMENTS

| 3,557,264 A * | 1/1971 | Getz et al. .................. 264/46.7 |
| 4,006,739 A | 2/1977 | Wahi |
| 4,061,898 A * | 12/1977 | Murray et al. ................ 219/211 |
| 4,189,182 A * | 2/1980 | Rhoe ........................ B60N 2/70 |
| | | 297/452.32 |
| 4,759,543 A * | 7/1988 | Feldman ............ A63B 23/0233 |
| | | 297/284.6 |
| 4,989,605 A | 2/1991 | Rossen |
| 5,007,633 A * | 4/1991 | Lemire ........................ 482/142 |
| 5,336,255 A * | 8/1994 | Kanare et al. ................ 607/149 |
| 5,409,500 A * | 4/1995 | Dyrek .......................... 607/111 |

(Continued)

*Primary Examiner* — Kaitlyn Smith
(74) *Attorney, Agent, or Firm* — Global Intellectual Property Agency, LLC; Daniel Boudwin

(57) ABSTRACT

A multi-layered therapy pad is provided having a comfortable and supportive structure that houses heat therapy and electrotherapy means for treating back injuries and sores while an individual lies thereon. The pad comprises a first and second outermost layer of low-resilience polyurethane foam sandwiching an internal layer of higher density foam, which also supports electrical connections between the therapy controller, the power source, and the two therapy means within the pad. The electrotherapy means comprises static or tethered electrodes that apply pulsing electric current directly onto the user's back for stimulation and easing of back pain, while the heat therapy is applied using a resistance heating element within the pad, which heats a majority of the pad for applying heat to the user's back. The operation of the therapy means is controlled by an external controller, while power in received through an external source or an internal battery pack.

2 Claims, 4 Drawing Sheets

(56) References Cited

U.S. PATENT DOCUMENTS

| | | | |
|---|---|---|---|
| 5,601,618 A * | 2/1997 | James | 607/71 |
| 6,728,577 B2 * | 4/2004 | Minogue et al. | 607/48 |
| 6,840,955 B2 * | 1/2005 | Ein | 607/108 |
| 7,328,470 B2 | 2/2008 | Harris, Jr. et al. | |
| 7,871,427 B2 * | 1/2011 | Dunbar et al. | 607/96 |
| 8,579,953 B1 * | 11/2013 | Dunbar et al. | 607/96 |
| 2002/0019654 A1 * | 2/2002 | Ellis | A61F 7/007 607/98 |
| 2003/0006640 A1 * | 1/2003 | Yasuda et al. | 297/452.35 |
| 2004/0133958 A1 * | 7/2004 | Darnell | A63B 71/10 2/15 |
| 2004/0210214 A1 * | 10/2004 | Knowlton | 606/41 |
| 2005/0043655 A1 * | 2/2005 | Schenck | 601/15 |
| 2005/0240121 A1 * | 10/2005 | Ferriss | A61B 5/1116 600/587 |
| 2006/0048282 A1 * | 3/2006 | Africa | A41D 1/084 2/267 |
| 2006/0052849 A1 * | 3/2006 | Docherty et al. | 607/100 |
| 2006/0142816 A1 * | 6/2006 | Fruitman et al. | 607/48 |
| 2006/0190057 A1 * | 8/2006 | Reese | 607/46 |
| 2007/0038165 A1 | 2/2007 | Trandafir et al. | |
| 2007/0142891 A1 * | 6/2007 | Stanley | 607/144 |
| 2007/0213646 A1 | 9/2007 | Han | |
| 2008/0033506 A1 * | 2/2008 | Flick | 607/50 |
| 2008/0255480 A1 * | 10/2008 | Lau | 601/15 |
| 2009/0216305 A1 * | 8/2009 | Bonner | 607/108 |
| 2009/0287264 A1 * | 11/2009 | Paret | 607/3 |
| 2009/0312676 A1 * | 12/2009 | Rousso et al. | 601/15 |
| 2010/0198321 A1 * | 8/2010 | Moeck | 607/107 |
| 2010/0211122 A1 * | 8/2010 | Hensley | 607/3 |
| 2010/0235997 A1 | 9/2010 | Jones | |
| 2011/0130796 A1 * | 6/2011 | Louise | 607/3 |
| 2012/0041488 A1 * | 2/2012 | Al Mubayadh | A61F 5/01 606/237 |
| 2014/0005759 A1 * | 1/2014 | Fahey et al. | 607/99 |
| 2014/0148879 A1 * | 5/2014 | Mersch | 607/90 |
| 2015/0094788 A1 * | 4/2015 | Pierenkemper | 607/96 |

* cited by examiner

MULTI-LAYERED HEAT THERAPY AND ELECTROTHERAPY BACK PAD DEVICE

CROSS REFERENCE TO RELATED APPLICATION

This application claims the benefit of U.S. Provisional Application No. 61/662,121 filed on Jun. 20, 2012, entitled "Ortho Neuro Sleep with Ezee." The above identified patent application is herein incorporated by reference in its entirety to provide continuity of disclosure.

BACKGROUND OF THE INVENTION

Field of the Invention

The present invention relates to a heat therapy and electrotherapy back pad that stimulates the nerves and muscles of the user's back to reduce pain and stiffness, while offering a comfortable and supportive structure upon which to lie upon. More specifically, the present invention pertains to a multi-layered back pad serving as a back support and heat therapy and electrotherapy device for a user, thereby treating back injuries, pain, and soreness It is common for individuals to experience back pain some time during their lives. Back pain can come about in a number of different ways and be a result of a number of different causes, including physical exertion, poor posture, the result of a physical injury, or as a result of individual medical issues that may make one more prone to back injury or soreness than others. The manifestation of back pain ranges from dull soreness to acute pain that can be nearly debilitating for the individual. In situations of acute pain, an individual may be bedridden for periods of time and prevented from engaging in normal activities. This makes rehabilitation activities difficult to initiate and less likely to succeed. Common remedies include the application of pain relieving medication, bed rest, and the use of physical supports for improved mobility. Each of these has their own specific drawbacks and hardships on the individual.

While physical therapy and updating one's behavior are the best ways to prevent and sometimes alleviate back pain in the long term, this does not address the real need for immediate relief of the affected area. The use of pain relieving medication serves as a temporary solution, but only masks the problem and gives rise to other concerns such as dependence and further injury to the back. A medicated individual may not realize they are exerting themselves in the moment, exacerbating an injury or causing more strain on the user's back. Swelling that may result, pinched nerves, or further straining of muscles can ensue that adversely affects the individual's recovery. The medicated user does not realize the pain and continues normal routines. This can be counterproductive to recovery, while the extended use of medication can lead to dependence on the medication, leading to other individual and public health concerns.

Therapeutic treatments for back injuries and back pain include heat therapy, electrotherapy, physical therapy, and the use of appliances that promote posture or remove stress on certain parts of the body. Heat therapy involves the application of a heat by a heat source to the affected area to relieve muscle tension and pain associated therewith. Generally a resistive heating element provides a consistent elevated temperature to the individual's back to loosen the muscles and relive tension. Electrotherapy can take on several forms, and generally concerns the application of electric current directly to the individual's muscles and nerves for stimulation and pain relief. Electrodes are connected to the user that connects to an electrical current source, which pulses the electric current for a period of time.

One such application is transcutaneous electrical nerve stimulation, or TENS, which is nerve excitation by pulsing application of electric current directly through the individual's skin at a given frequency. The stimulation has therapeutic effects and its application is non-invasive, providing a solution that offers pain management, increased blood flow, and relaxation of muscle soreness and spasms. The final form of therapy that is most helpful is physical therapy, which involves the controlled exercise of the muscles groups of the back and other body regions for strengthening the individual and reducing stiffness. The present invention pertains to the application of both heat therapy and electrotherapy in a supportive and comfortable back pad device.

Physical appliances are supportive structures that position an individual in the proper posture or support the user properly while in different positions, either to prevent back injury or to provide therapeutic relief thereto. Proper positioning and support of one's back is essential to reducing back pain, preventing injuries, and further for treating injuries after the fact. The present invention provides a back pack having a supportive and comfortable structure that supports a user in a supine position, while at the same time applying heat therapy and electrotherapy to the user's back in a way to relieve muscle stress, treat pain, stimulate nerves, and promote proper posture while lying down.

The present invention relates to a back pad appliance upon which a user rests in a supine position, wherein the pad provides a comfortable and supportive surface having both a defined structure and imbedded therapeutic devices. Within the pad are several layers for comfort and support, along with therapy means that are directly apply treatment to individuals suffering from back pain. These therapy means include a resistive heating element that applies heat therapy to the back region of the user, while electrodes of the electrotherapy means are applied to the user's back for the application of electrical current or pulses thereof. The overall goal is to provide a back pad that can be used in the home and in bed for back pain relief, accelerating recovery of back injuries or treating back pain without the use of pain killing medication.

Description of the Prior Art

Devices have been disclosed in the prior art that relate to pain relieving and therapeutic devices. These include devices that have been patented and published in patent application publications, and generally relate to pads, pillows, and other structures having various user stimulation and therapy means. The following is a list of devices deemed most relevant to the present disclosure, which are herein described for the purposes of highlighting and differentiating the unique aspects of the present invention, and further highlighting the drawbacks existing in the prior art.

Specifically, U.S. Pat. No. 7,328,470 to Harris discloses a seat-less massaging bed cushion having a backrest and armrest portion for supporting a user in a seated position. Within the backrest is at least one massage unit that may include pulsing transducers or heating units controlled by a control panel and provided electrical power via a power supply. The pulsing transducers and heating units provide a massaging backrest that relieves pain and massages the user while in a seated position. While disclosing a heating and massaging therapeutic device, the Harris device fails to disclose the functional and design aspects of the present invention, notably a heat therapy and electrotherapy device for a prone user recovering from a back injury or treating a sore back during periods of rest.

U.S. Patent Application Publication No. 2007/0213646 to Han discloses a pillar-shaped pillow having a massaging capability. The pillow includes a vibration motor and a negative ion generating portion, both elements providing therapeutic benefits for the neck and scalp region of a user lying on the pillow. Similar to the Harris device, the Han device provides a massaging and therapeutic device for relaxation and muscle treatment, but fails to disclose the novel aspects of the heating and electrotherapy pad of the present invention.

The present invention describes a back treatment pad having a supportive structure, a heat therapy means, and an electrotherapy means, whereby the assembly is used to support a supine user. It is submitted that the present invention substantially diverges in design elements from the prior art, and consequently it is clear that there is a need in the art for an improvement to existing back therapy support devices. In this regard the instant invention substantially fulfills these needs.

SUMMARY OF THE INVENTION

In view of the foregoing disadvantages inherent in the known types of back therapy pad supports now present in the prior art, the present invention provides a new therapy pad that can be utilized for providing convenience for the user when supporting the user in a comfortable and supportive supine position while applying heat therapy and electrotherapy thereto.

It is therefore an object of the present invention to provide a new and improved back therapy support device that has all of the advantages of the prior art and none of the disadvantages.

It is another object of the present invention to provide a back therapy support device that includes outer layers of softer foam material sandwiching an inner core of denser foam material, along with an upper surface design that accommodates the back geometry of a user for both support and comfortable resting of a supine user thereon.

Another object of the present invention is to provide a back therapy support device that includes a heat therapy means, whereby a resistive heating element is embedded within the core of the pad and provides a means of transferring heat into the user's back for muscle tension and pain relief.

Yet another object of the present invention is to provide a back therapy support device that includes an electrotherapy means, whereby a plurality of electrodes are positioned along the upper surface of the mat to applying a pulsating electric current to the user through direct skin contact for nerve and muscle stimulation and pain relief.

Another object of the present invention is to provide a back therapy support device that includes an external controller for the user to adapt the intensive of the therapy means, including the temperature of the heating element and the amplitude or frequency of the electrical stimulation pulses.

A final object of the present invention is to provide a back therapy support device that can be used in the home or while traveling to treat back pain and soreness while the user rests against the pad in a supine position.

Other objects, features and advantages of the present invention will become apparent from the following detailed description taken in conjunction with the accompanying drawings.

BRIEF DESCRIPTIONS OF THE DRAWINGS

Although the characteristic features of this invention will be particularly pointed out in the claims, the invention itself and manner in which it may be made and used may be better understood after a review of the following description, taken in connection with the accompanying drawings wherein like numeral annotations are provided throughout.

DETAILED DESCRIPTION OF THE INVENTION

Figure 1:
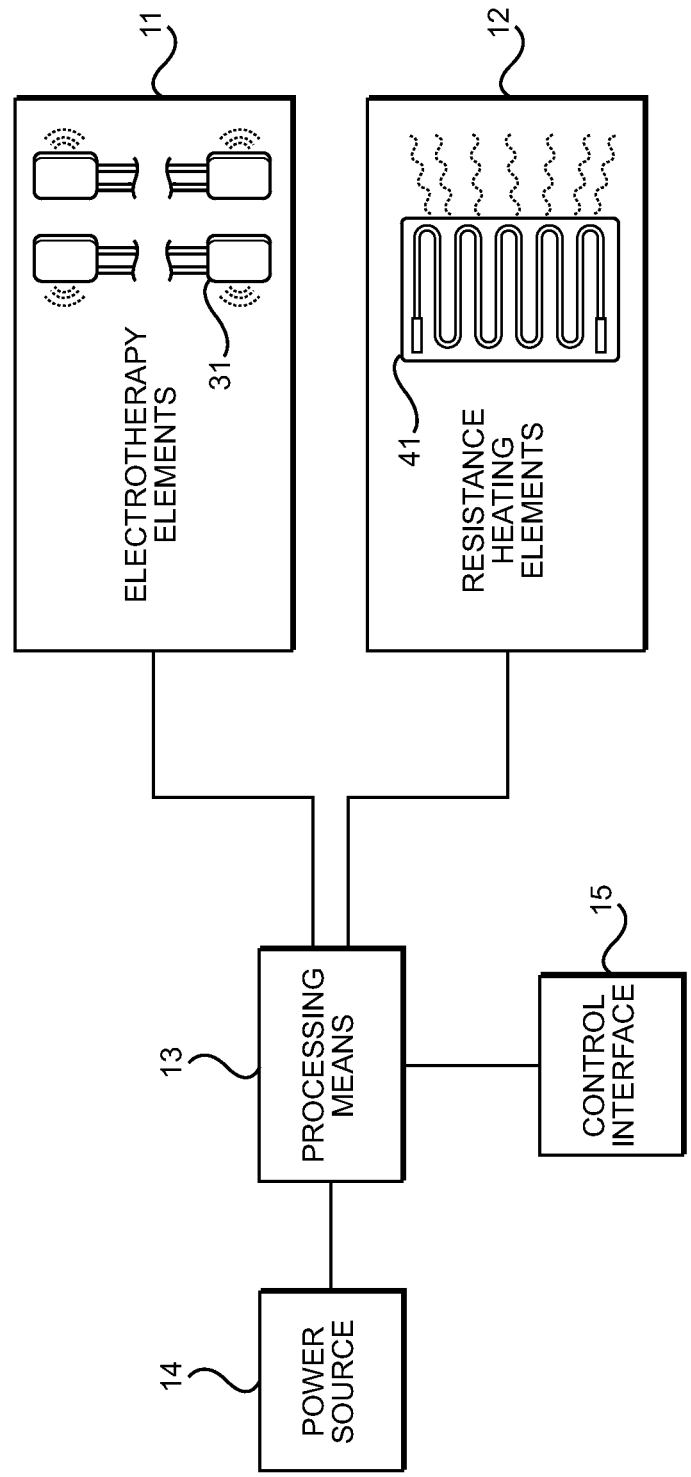
FIG. 1 shows a system diagram of the operational and therapy elements of the present invention.

Reference is made herein to the attached drawings. Like reference numerals are used throughout the drawings to depict like or similar elements of the back therapy pad device. For the purposes of presenting a brief and clear description of the present invention, the preferred embodiment will be discussed as used for treating individuals with sore and injured backs. The figures are intended for representative purposes only and should not be considered to be limiting in any respect.

Referring now to FIG. 1, there is shown a system diagram of the therapy elements of the present invention. The present invention provides a back pad support with embedded therapy means, including an electrotherapy means 11 and a heat therapy means 12. The heat therapy means comprises a resistive heating element 41 that transforms electrical resistance into thermal energy that is dissipated into the pad and transferred into the user's back. The heating elements 41 is preferably a surface within the back pad having an elongated resistive heating element creating a path within the pad, whereby heat generated from the elongated element is given off largely uniformly from the pad such that the pad in proximity to the heating means increases in temperature.

Driving the resistive heating element 41 is an electric circuit controlled by a logic circuit or processing means 13, which derives electrical power from an electrical power source 14 and input from a user control interface 15. The processing means may comprise a microprocessor, a logic circuit, or a central processing unit (CPU), which interprets inputs from the user interface 15, and controls the output from the electrotherapy 11 and heat therapy means 12. It is not desired to limit the present invention to a specific controller or processing means, but rather to disclose an assembly that is capable of receiving inputs from a user and controlling the output from different therapy means within the back pad for different levels and types of treatment.

The electrotherapy means 11 comprises a plurality of electrodes 31, which are pads having electrical leads. The leads are connected directly to a user's skin, and electrical current at a given amplitude and frequency are pulsed through the leads for stimulation of the user's back muscles and nerves. The preferred embodiment of the electrotherapy is TENS, which provides for either sensory stimulation or motor contraction of the user's muscles, depending on the chosen frequency and amplitude, which determines the intensity of the therapy. Electrical current is pulsed through the leads and controlled by the processing means, whereby current from the power source is transformed and directed to the leads at the desired intensity.

The control interface is a tethered or remote interface (such as a remote control), which offers to the user a variety of options when lying on the pad. First, the user can choose to activate either or both of the therapy means. Thereafter, the intensity of both can be controlled, whereby the thermal output of the heating element 41 is controlled and the intensity of the electrotherapy pulses is selected. In its inactive form, when both therapy means are deactivated, the pad offers a comfortable, supportive, and conforming structure to support a user experiencing back pain or discomfort.

Figure 2:
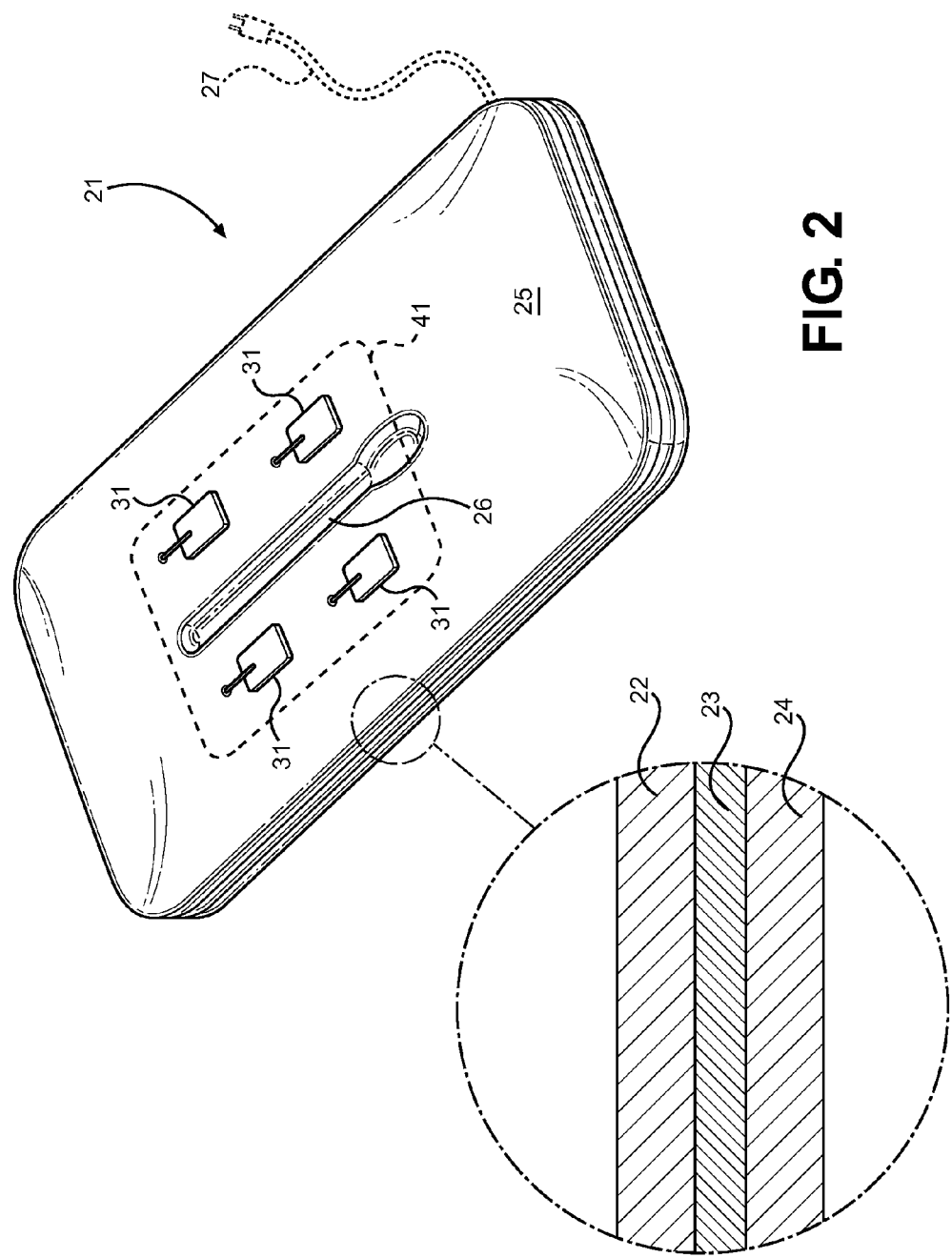
FIG. 2 shows a perspective view and cross section of the present therapy pad of the present invention.

Referring now to FIG. 2, there is shown a perspective view of the present invention and a cross section through the pad surface to visualize its construction. The device comprises an elongated pad 21 having an upper surface 25 upon which a user rests in the supine position. The back of the user is pressed thereagainst and into a contoured area 26 adapted to support and form to his or her spine. The thickness of the pad 21 is comprised of multiple layers that provide specific treatment and support the user. The thickness is comprised of a lowermost layer 24, an uppermost layer 22, and a sandwiched layer 23 therebetween. The lowermost and uppermost layers 22, 24 are comprised of a low-resilience polyurethane foam material, memory foam, or similar low resistance and highly deformable material type that affords cushioned support of the user. The sandwiched layer 23 comprises a higher density foam material that supports the operation elements of the therapy means, including the heating elements 41 and all electrical connections.

Along the upper surface 25 of the pad 21 are a plurality of electrotherapy electrodes 31 that are either statically supported along the pad upper surface 25 or are tether thereto by lead wires. If tethered, the electrodes can be attached to the user's back prior to lying on the pad 21. If the electrodes 31 are statically supported along the pad upper surface 25, the user can simply adjust his or her position on the pad 21 to position the electrodes in the affected area requiring therapy. Further still, the control interface of the present invention can be utilized to choose which of the electrodes to activate, focusing therapy to those specific areas, or all of the application areas desired by the user. Power for the therapy means is preferably provided by an external power source, such as a wall outlet accessed by way of an electrical cord 27. Alternatively, the pad may include a battery pack, which supplies required electrical power for a period of time before charging or replenishment periods. The alternate power source is one that is ideally suited for those who travel and are not frequently using the device near a power outlet.

Figure 3:
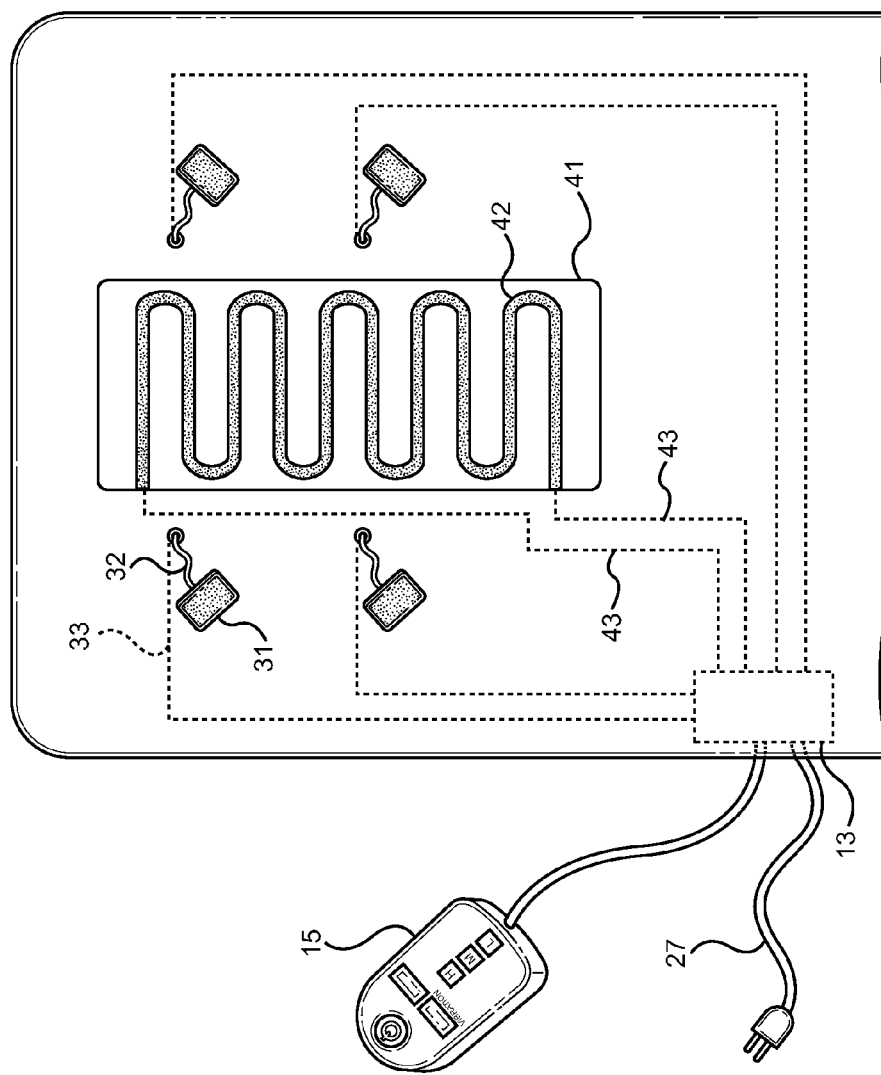
FIG. 3 shows an internal schematic view of the present invention.

Referring now to FIG. 3, there is shown a schematic view of the present invention and its connections within the interior of the pad. As shown, the processing means 13 is a central hub or housing within the pad that accepts power from an external source 27, receives input from a controller 15, and distributes electrical power through connections 43, 33 to the heat therapy means and electrotherapy means within the pad. Wired connections 33 between the processing means 13 an the electrodes 31 provide a conduit for the outgoing electrical pulses, while the wired connection 43 of the heat therapy means provides electrical current to the heating elements 42 within the heating pad 41. The electrodes may be statically secured to the pad, or tethered 32 thereto to allow the electrodes 31 to be applied to the individual before lying down. The layout of FIG. 3 is merely a schematic representation of the system element connections and their routing within the interior of the pad. It is not desired to limit the present invention to a given electrical architecture or wiring layout, but rather it is desired to display a representative wiring diagram that accomplishes the tasks of the present invention herein described.

Figure 4:
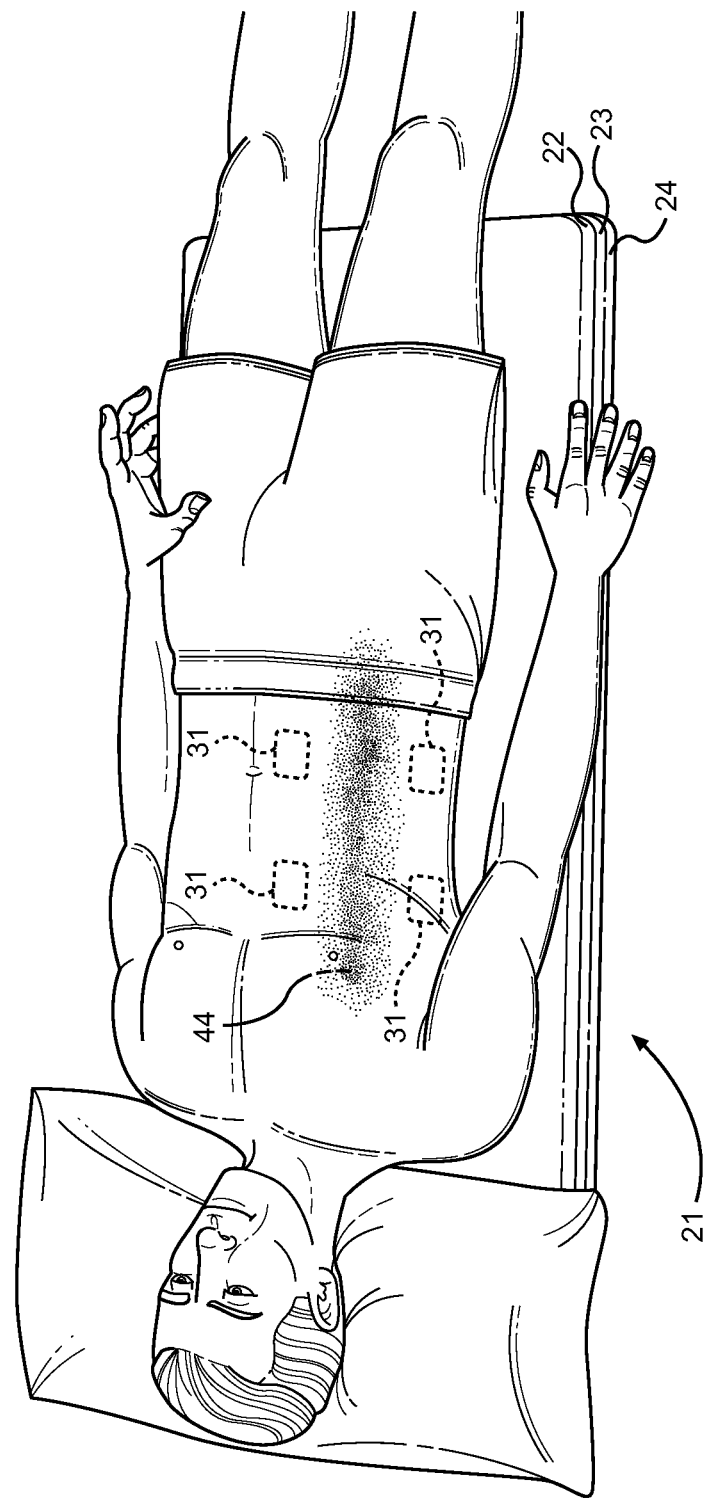
FIG. 4 shows a view of the present invention in a working state.

Referring now to FIG. 4, there is shown a view of the present invention in a working state, applying both heat therapy and electrotherapy to a supine user on the mat 21. As shown, the user rests on the uppermost layer 22 of the mat, while the sandwiched 23 and lowermost 24 layer support the user and the working elements of the device. The resistive heating element of the heat therapy means dissipates heat 44 from the pad 21 to the user, while the electrodes 31 of the electrotherapy means pulsate against the user's skin to stimulate nerve activates and muscle contraction. The user can rest against the pad as it support him, while the therapy means apply heat 44 and pulsating electrical input directly to the user's back for relieving pain, reducing injury recovery time, and for treating back soreness.

Many people suffer from back aches and pains on a daily basis. If a person has a particularly stressful job, he or she may experience muscle spasms that make it difficult to be productive both at work and at home. Some people take medication, but pills may cause unpleasant side effects or make users drowsy at inopportune times. The present invention provides relief for such individuals in the form of a therapeutic pad. The device comprises a pad made of several supportive foam layers that conform to the contours of the user's spine, while imbedded heat therapy and electrotherapy means treat the user's back to reduce pain and treat injuries. The device can be deployed on any flat surface, while the therapy means are controlled by the user to offer the relief desired. It is contemplated that the present invention may be used for periods of relaxation, for treatment of back problems after a day of work, or event for a user trying to sleep while suffering from back pain.

It is submitted that the instant invention has been shown and described in what is considered to be the most practical and preferred embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:
1. A therapeutic back pad device, comprising:
   an elongated pad thickness;
   wherein said pad thickness comprise, a lowermost layer, an uppermost layer, and a sandwiched layer therebetween;
   said lowermost and uppermost layer comprising a low-resilience polyurethane foam material;

said sandwiched layer comprising a foam material of higher density than said uppermost and lowermost material;
wherein said uppermost layer comprises an upper surface adapted to receive a user thereon;
a heat therapy means within said pad thickness for applying heat to said user in a supine position on said upper surface of said uppermost layer;
said heat therapy means comprising a resistive heating element;
an electrotherapy means within said pad thickness of said elongated pad for applying electrical current to said user;
said electrotherapy means comprising at least one electrode;
a processing means and electrical connections to said resistive heating element and said electrodes;
a power source;
a control interface for controlling said processing means; and
wherein said upper surface further comprises a recessed area that conforms to the spine of the user's back.

2. A therapeutic back pad device, comprising:
an elongated pad having a thickness, an upper surface, and a lower surface;
a heat therapy means within said pad thickness for applying heat to a user in a supine position on said pad upper surface;
wherein said pad upper surface further comprises a recessed area that conforms to the spine of a user's back;
said heat therapy means comprising a resistive heating element;
an electrotherapy means within said pad thickness for applying electrical current to a said user;
said electrotherapy means comprising at least one electrode;
a processing means and electrical connections to said resistive heating element and said electrodes;
a power source;
a control interface for controlling said processing means.

* * * * *